(12) United States Patent
Tsukada et al.

(10) Patent No.: US 7,048,193 B2
(45) Date of Patent: May 23, 2006

(54) MOTORIZED INFUSION INJECTION SYSTEM

(75) Inventors: Osamu Tsukada, Nagano (JP); Yasuhiko Nakajima, Kanagawa (JP)

(73) Assignee: Tsukada Medical Research Co., Ltd., Tokyo (JP)

( * ) Notice: Subject to any disclaimer, the term of this patent is extended or adjusted under 35 U.S.C. 154(b) by 22 days.

(21) Appl. No.: 10/491,982

(22) PCT Filed: Apr. 2, 2003

(86) PCT No.: PCT/JP03/04224

§ 371 (c)(1),
(2), (4) Date: Apr. 7, 2004

(87) PCT Pub. No.: WO2004/089445

PCT Pub. Date: Oct. 21, 2004

(65) Prior Publication Data

US 2004/0238618 A1   Dec. 2, 2004

(51) Int. Cl.
*G06K 19/00* (2006.01)

(52) U.S. Cl. .................. 235/487; 235/375; 235/376; 235/492

(58) Field of Classification Search .............. 235/487, 235/375, 376, 492, 493; 604/151, 186, 189; 700/213, 225, 235; 705/3
See application file for complete search history.

(56) References Cited

U.S. PATENT DOCUMENTS

| | | | | |
|---|---|---|---|---|
| 4,291,692 A | * | 9/1981 | Bowman et al. | 604/31 |
| 4,827,112 A | * | 5/1989 | Yoshino et al. | 235/380 |
| 5,078,683 A | * | 1/1992 | Sancoff et al. | 604/67 |
| 5,104,374 A | * | 4/1992 | Bishko et al. | 604/31 |
| 5,378,231 A | * | 1/1995 | Johnson et al. | 604/67 |
| 5,651,775 A | * | 7/1997 | Walker et al. | 604/207 |
| 5,781,442 A | * | 7/1998 | Engleson et al. | 700/214 |
| 6,519,569 B1 | * | 2/2003 | White et al. | 705/3 |
| 6,551,276 B1 | * | 4/2003 | Mann et al. | 604/131 |
| 6,790,198 B1 | * | 9/2004 | White et al. | 604/151 |
| 6,872,200 B1 | * | 3/2005 | Mann et al. | 604/890.1 |
| 6,936,029 B1 | * | 8/2005 | Mann et al. | 604/131 |

FOREIGN PATENT DOCUMENTS

| | | | |
|---|---|---|---|
| JP | 05220221 A | * | 8/1993 |
| JP | 6-277283 A | | 10/1994 |
| JP | 2002-1195887 A | | 4/2002 |
| JP | 2002-282338 A | | 10/2002 |
| WO | WO 98/19734 A1 | | 5/1998 |
| WO | WO 2004/089445 A1 | | 10/2004 |

* cited by examiner

Primary Examiner—Thien M. Le
Assistant Examiner—Kimberly D. Nguyen
(74) Attorney, Agent, or Firm—Sughrue Mion, PLLC

(57) ABSTRACT

A motorized infusion injection system having an information card record side unit 10 and an information card user side unit 20. Unit 10 includes an information card 11 on which medication information is written for a patient, a reader/writer 12 that can read/write the medication information from/on the information card 11, and an input 13 for inputting the medication information. Unit 20 includes a reader 21 for reading out information from the information card 11, an input 22 for inputting personal information of a patient and a controller 23 to generate a medication signal. A transducer 24 receives the medication signal and transduces the medication signal to a mechanical signal, and a motorized PCA pump 25 connected to an infusion storing-container 30 that contains a given infusion 31 and to an injector 40 that injects the infusion into a body of the patient for supplying the infusion 31 from the infusion storing-container 30 to the injector 40.

4 Claims, 6 Drawing Sheets

MOTORIZED INFUSION INJECTION SYSTEM

FIELD OF THE INVENTION

This invention relates to a motorized infusion injection system and more particularly relates to a motorized infusion injection system utilizing a motorized PCA (Patient-Controlled Analgesia) pump.

BACKGROUND OF THE INVENTION

In the field of postoperative pain control, pain clinic, emergency medical treatment, or the like, an infusion is injected into a body of a patient by utilizing a non-motorized continuation injector or a motorized PCA pump. Such infusion includes an analgesic agent, carcinostatic agent, a nutrition agent, a physiological saline, and the like. There are various types of the PCA pumps in domestic products and foreign products. The PCA pump in the foreign products is relatively expensive and has drawbacks in operation and display indication. On the contrary, the PCA pump in the domestic products is relatively inexpensive and generally favorable in operation and display indication. However, the domestic products lack in uniformity of product standard, since fabricants produce the PCA pumps on the basis of their unique standards.

Information to be inputted in the PCA pump includes a kind of an infusion, an amount of injection, a period in time for injection, a flow rate for injection, and the like. Human errors have often occurred in association with alterations of models, a medication chart, a handler, or the like.

SUMMARY OF THE INVENTION

Accordingly, an object of the present invention is to provide an infusion injection system that is not affected by a unique standard of a fabricant and can eliminate a human error of a handler.

A motorized infusion injection system of the present invention comprises an information card record side unit and an information card user side unit. The information card record side unit includes an information card on which medication information is written in accordance with a case of a patient, a reader/writer that can read/write the medication information from/on the information card, and an input means for inputting the medication information into the reader/writer. The information card is selected from one of a magnetic card, an IC card, and an optical card.

The information card user side unit includes a reader for reading out information from the information card, an input means for inputting personal information of a patient into the unit, a controller for receiving the medication information from the reader and the personal information from the input means of the user side unit to generate a medication signal, a transducer for receiving the medication signal from the controller to transduce the medication signal to a mechanical signal, and a motorized PCA pump connected to an infusion storing-container that contains a given infusion and to an injector that injects the infusion into a body of the patient for supplying the infusion from the infusion storing-container to the injector.

PREFERRED EMBODIMENTS OF THE INVENTION

Figure 1:
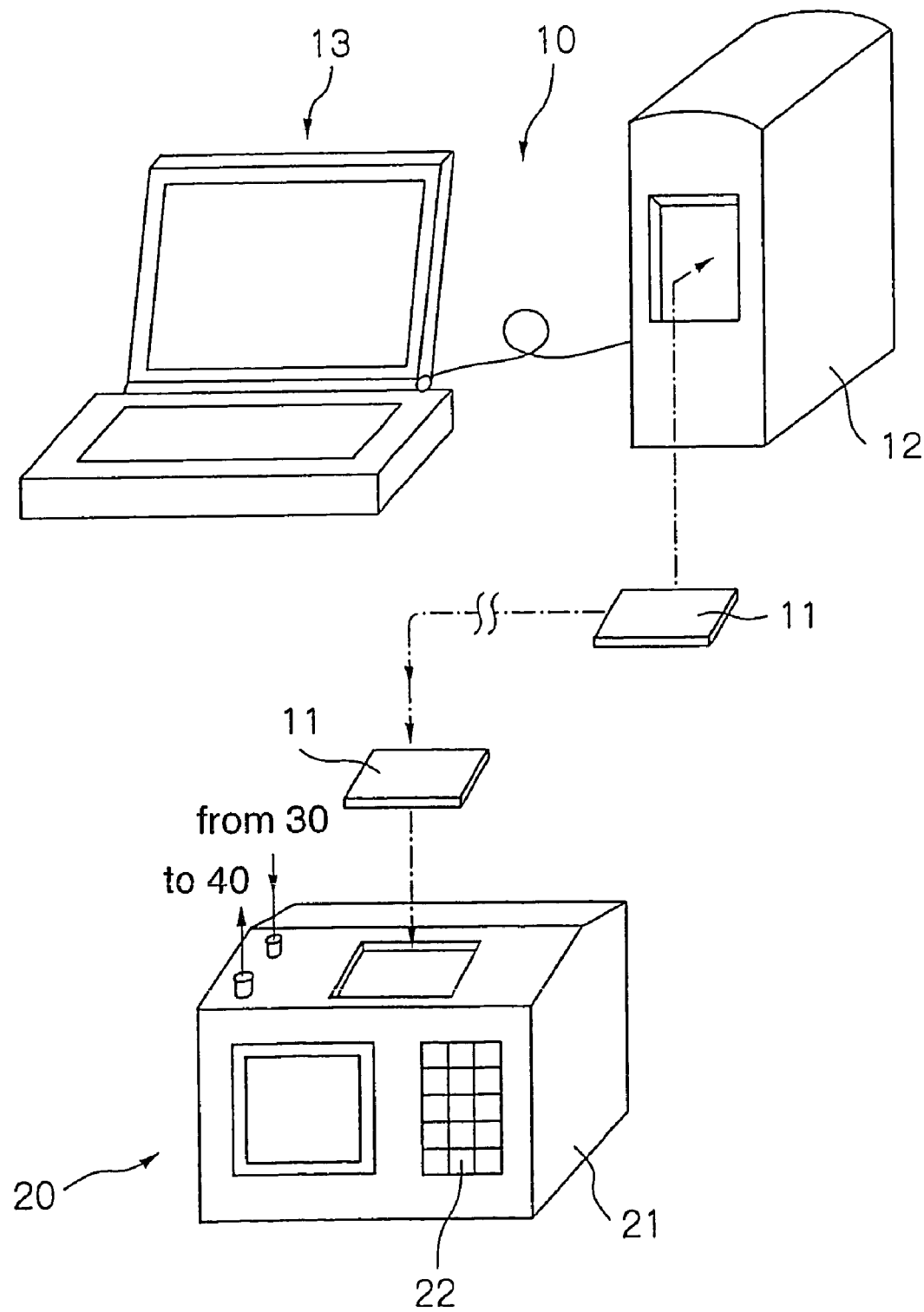
FIG. 1 is a schematic construction explanatory view of an infusion injection system in accordance with the present invention.

Referring now to the drawings, a preferred embodiment of a motorized infusion injection system in accordance with the present invention will be described below.

As shown in FIG. 1, a motorized infusion injection system of the present invention comprises an information card record side unit 10 and an information card user side unit 20.

Figure 3:
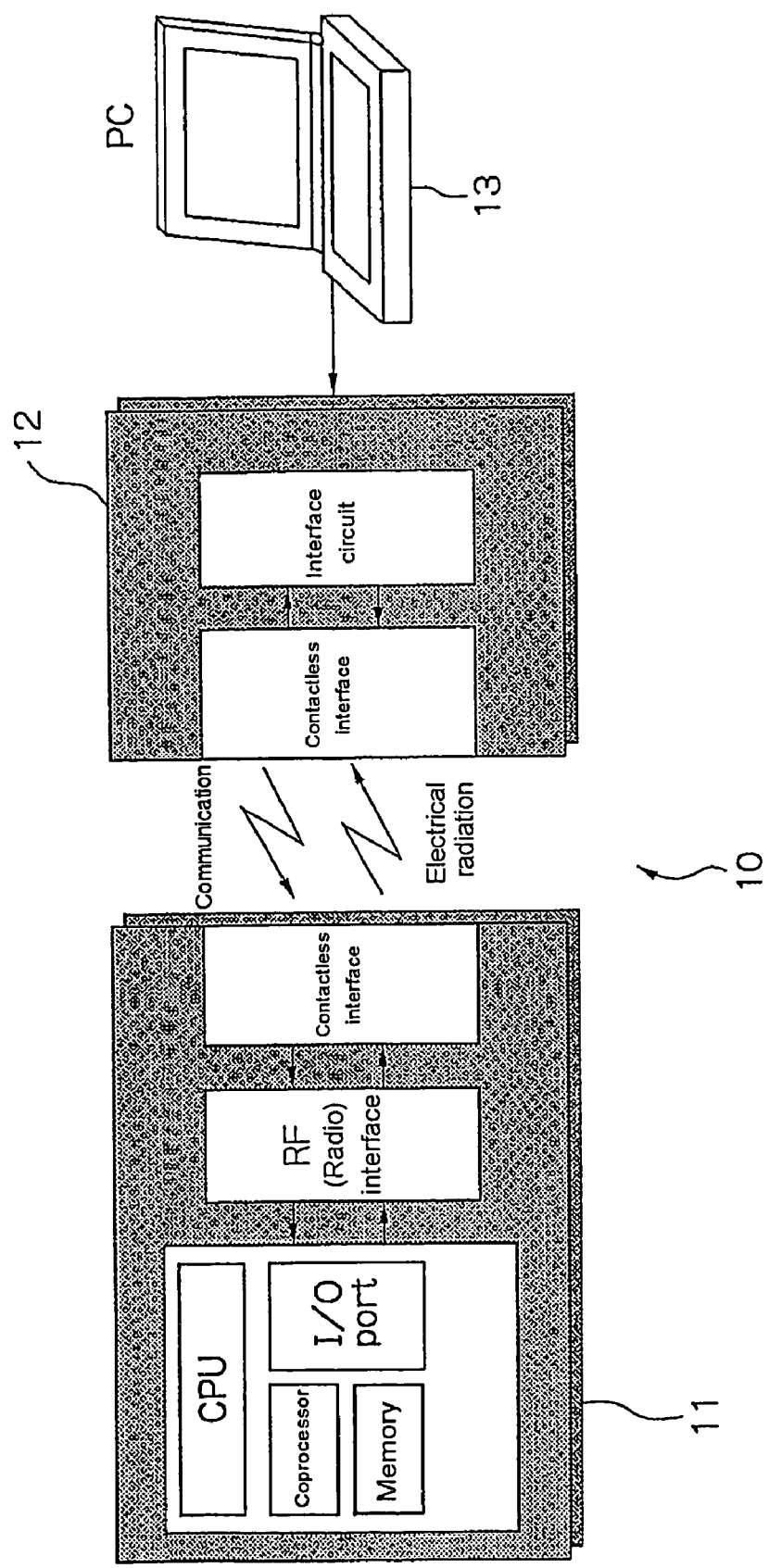
FIG. 3 is a schematic diagrammatical explanatory view of an information card record side unit in the infusion injection system of the present invention.

The information card record side unit 10, as shown in FIGS. 1 and 3, includes an information card 11 on which medication information is written in accordance with a case of a patient, a reader/writer (R/W) 12 that can read/write the medication information from/on the information card 11, and an input means 13 for inputting the medication information into the reader/writer 12. The information card 11 is selected from one of a conventional magnetic card, a conventional IC card, and a conventional optical card. The input means 13 may be a conventional personal computer (PC). For the sake of convenience of explanation, a conventional IC card is used as the information card 11 in the embodiment of the infusion injection system of the present invention.

As shown in FIG. 3, the IC card (information card) 11 includes a CPU, a coprocessor, a memory, an I/O port, a RF (radio) interface, and a contactless interface. As shown in FIG. 3, the reader/writer (R/W) 12 includes a contactless interface and an interface circuit. The IC card 11 and the reader/writer 12 are communicated with each other through electrical radiation.

Figure 4:
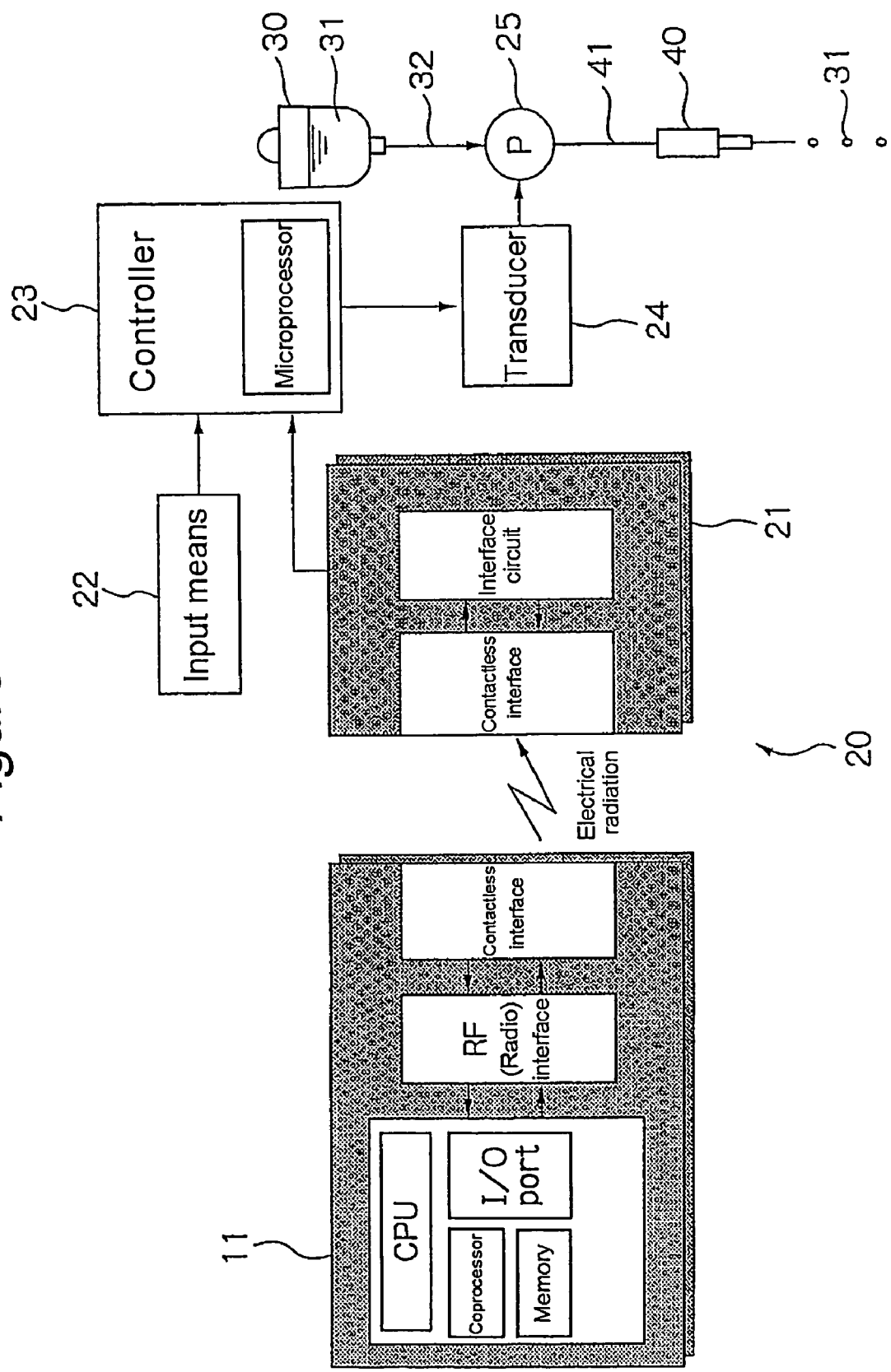
FIG. 4 is a schematic diagrammatical explanatory view of an information card user side unit in the infusion injection system of the present invention.

The information card user side unit 20, as shown in FIGS. 1 and 4, includes a reader (R) 21 for reading out information from the IC card (information card) 11, an input means 22 for inputting personal information of a patient, a controller 23 for receiving the medication information from the reader 21 and the personal information from the input means 22 to generate a medication signal, a transducer 24 for receiving the medication signal from the controller 23 to transduce the medication signal to a mechanical signal, and a motorized PCA pump 25 connected to an infusion storing-container 30 that contains a given infusion 31 and to an injector 40 that injects the infusion 31 into a body of a patient 50 (FIG. 2) for supplying the infusion 31 from the infusion storing-container 30 to the injector 40.

The reader (R) 21, as shown in FIGS. 1 and 4, includes a contactless interface and an interface circuit. The IC card 11 and the reader 21 are communicated with each other through electrical radiation. Although the input means 22 is a ten key in the illustrated embodiment, it may be a conventional PC. The controller 23 includes a microprocessor. The transducer 24 and the motorized PCA pump 25 may be conventional types.

Figure 5:
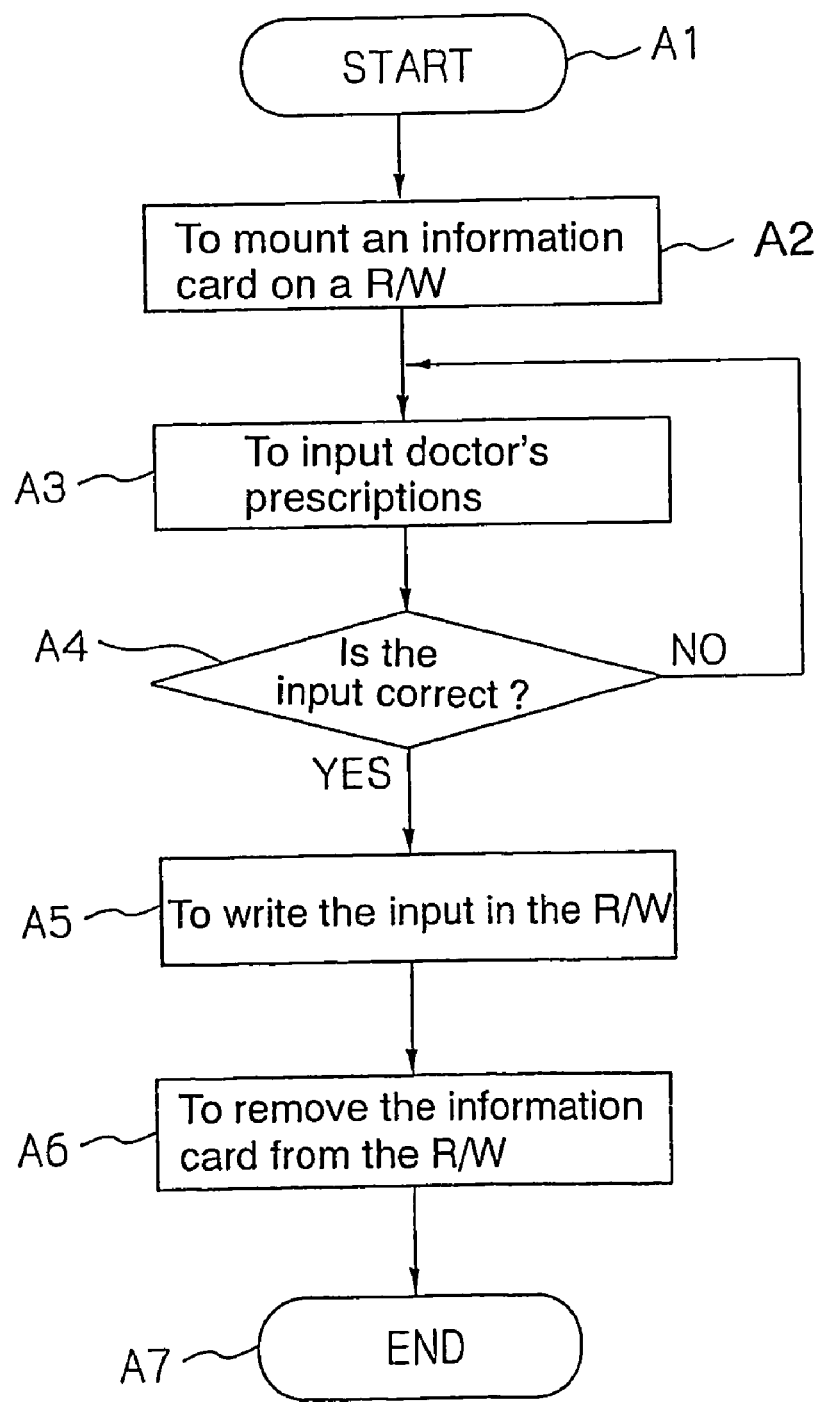
FIG. 5 is a flow chart that illustrates an operation of the information card record side unit in the infusion injection system of the present invention.

Referring to a flow chart shown in FIG. 5, an operation of the information record side unit 10 in the infusion injection system of the present invention will be described below.

Firstly, the information record side unit 10 is started (step A1). Secondly, the information card (IC card) 11 is mounted on the reader/writer 12 (step A2). The input means (PC) 13 inputs doctor's prescriptions (for example, a kind of infusion, an amount of injection, a period in time of injection, a flow rate, and the like) that are made in accordance with a case of a patient into the reader/writer 12 (step A3). In the step A3, personal information of a patient (for example, passwords of a patient, a name of the patient, a birthday of the patient, and the like) is also inputted in the reader/writer 12. An assessment is made as to whether the input is correct or not (step A4). If the input is not correct, the step A4 is returned to the step A3 and the input means 13 inputs the doctor's prescriptions again. If the input is correct, the doctor's prescriptions are written in the reader/writer (R/W) 12 (step A5). The information card (IC card) 11 is removed from the reader/writer (R/W) 12 (step A6). Finally, the unit 10 is ended (step A7).

Figure 6:
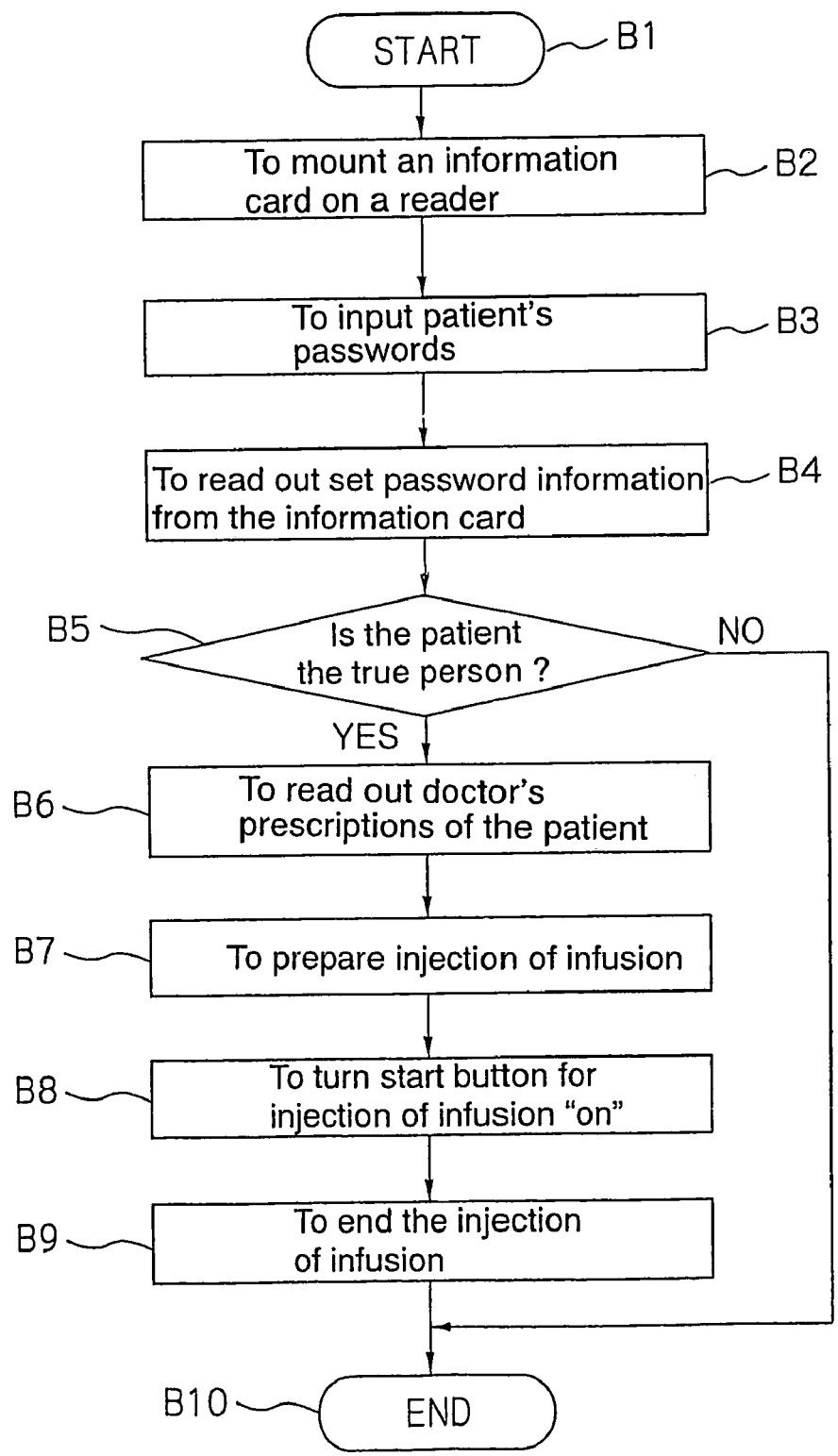
FIG. 6 is a flow chart that illustrates an operation of the information card user side unit in the infusion injection system of the present invention.

Next, referring to a flow chart shown in FIG. 6, an operation of the information card user side unit 20 in the infusion injection system of the present invention will be described below.

Firstly, the information card user side unit 20 is started (step B1). Secondly, the information card (IC card) 11 is mounted on the reader (R) 21 (step B2). The input means 22 inputs passwords of a patient into the controller 23 (step B3). The controller 23 reads out set password information (personal information) from the information card (IC card) 11 (step B4). Confirmation is made as to whether or not a patient is a true person on the basis of the set personal information (step B5). If the patient is not the true person, the step B5 is ended (step B10). If the patient is the true person, the reader 21 reads out the doctor's prescriptions of the patient from the IC card 11 (step B6). A given infusion storing-container 30 and a given injector 40 are prepared (step B7). A start button for infusion injection is turned to "ON" (step B8). Then, an infusion 31 is delivered from the injector 40. After removing air bubbles from the injector 40, the injector 40 is attached to the patient 50 and the infusion 31 is continuously injected into the body of the patient 50. After a given amount of infusion 31 is injected into the patient, the injection of infusion is ended (step B9). Finally, the unit 20 is ended (step B10).

Figure 2:
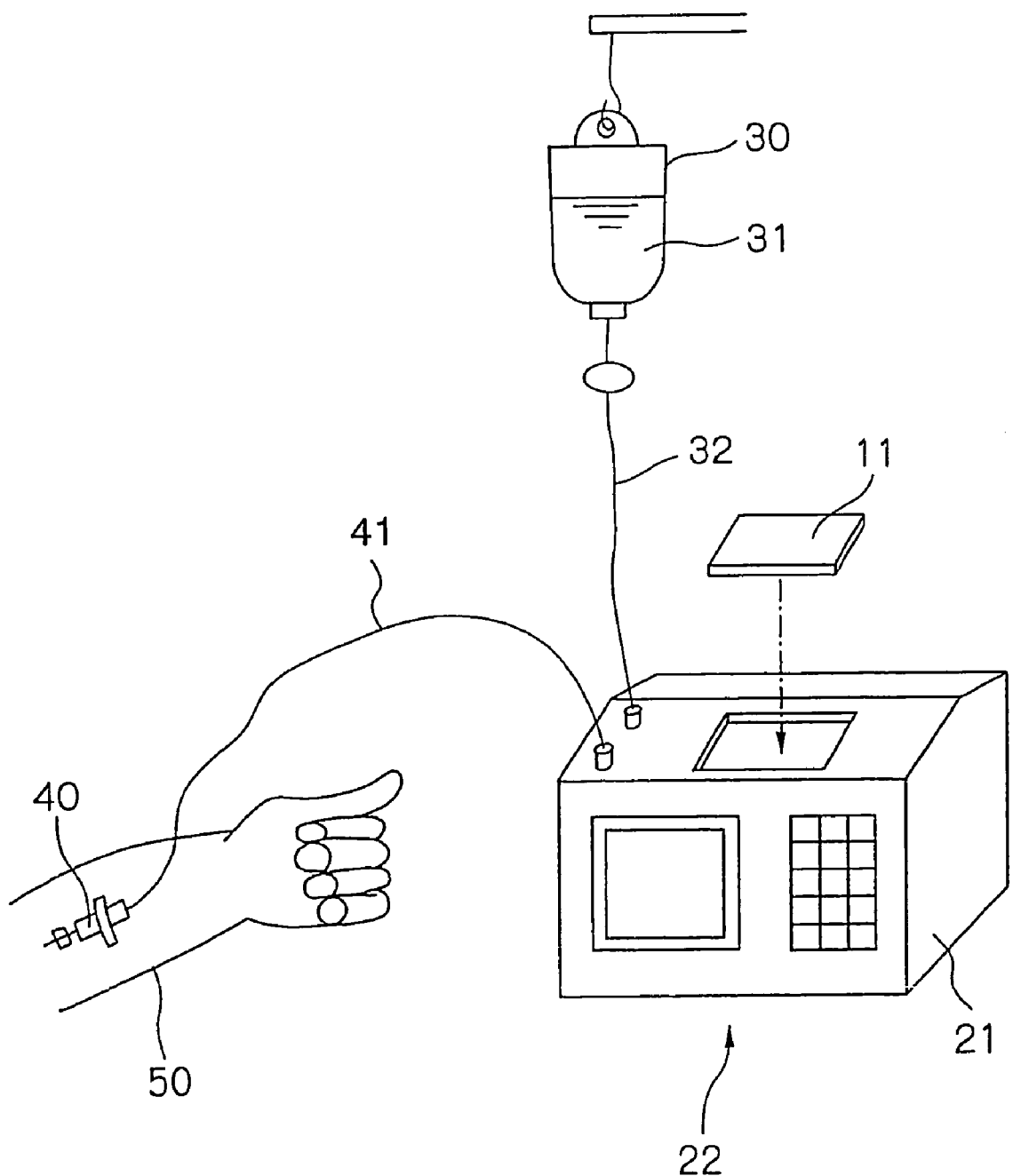
FIG. 2 is a schematic explanatory view of the infusion injection system of the present invention, illustrating an example of the system in use.

FIG. 2 is a schematic explanatory view of the infusion injection system of the present invention, illustrating an example of the system in use. The information card (IC card) 11 is mounted on the reader 21 in the information card user side unit 20. The infusion storing-container 30 and injector 40 are connected through conduits 32 and 41 to the motorized PCA pump 25 (FIG. 4). The injector 40 is attached to a given portion of the patient 50 (left arm in the illustrated embodiment) and the infusion is injected continuously.

The patient may carry the information card 11, or it may be secured to and sealed in the information card user side unit 20.

POSSIBILITY OF UTILIZATION IN AN INDUSTRIAL FIELD

The infusion injection system of the present invention can be generally utilized in medical care organizations, urgent facilities, care giving organizations, domestic homes, or the like.

The invention claimed is:

1. A motorized infusion injection system comprising an information card record side unit, and at least one information card user side unit, said information card user side unit being physically separate from said information card record side unit;
    said information card record side unit being adapted to communicate with an information card on which medication information is written in accordance with a case of a patient and comprising, a reader/writer that can read/write said medication information from/on said information card, and an input means for inputting said medication information into said reader/writer; and
    said at least one information card user side unit being adapted to communicate with said information card and comprising a reader for reading out information from said information card, an input means for inputting personal information of a patient into said information card user side unit, a controller for receiving said medication information from said reader and said personal information from said input means of said user side unit to generate a medication signal, a transducer for receiving the medication signal from said controller to transduce said medication signal to a mechanical signal, and a motorized Patient Controlled Analgesia pump, said pump being adapted for connection to an infusion storing-container that contains a given infusion and to an injector that injects said infusion into a body of the patient for supplying said infusion from said infusion storing-container to said injector.

2. An infusion injection system according to claim 1 further comprising an information card coupled to at least one of said units.

3. An infusion injection system according to claim 2 wherein said information card is selected from one of a magnetic card, an IC card, and an optical card.

4. An infusion injection system according to claim 1 further comprising an infusion storing-container that contains a given infusion and to an injector that injects said infusion into a body of the patient for supplying said infusion from said infusion storing-container to said injector.

* * * * *